United States Patent
Royer

(10) Patent No.: US 11,719,645 B2
(45) Date of Patent: Aug. 8, 2023

(54) REDUCING AGENT FOR ARSENIC MEASUREMENT

(71) Applicant: Hach Company, Loveland, CO (US)

(72) Inventor: Douglas F. Royer, Gilbert, IA (US)

(73) Assignee: HACH COMPANY, Loveland, CO (US)

( * ) Notice: Subject to any disclaimer, the term of this patent is extended or adjusted under 35 U.S.C. 154(b) by 236 days.

(21) Appl. No.: 17/345,359

(22) Filed: Jun. 11, 2021

(65) Prior Publication Data

US 2022/0397534 A1    Dec. 15, 2022

(51) Int. Cl.
*G01N 21/78*    (2006.01)
*G01N 33/18*    (2006.01)

(52) U.S. Cl.
CPC ............. *G01N 21/78* (2013.01); *G01N 33/18* (2013.01)

(58) Field of Classification Search
CPC .............................. G01N 21/78; G01N 33/18
See application file for complete search history.

(56) References Cited

U.S. PATENT DOCUMENTS

| 6,696,300 B1 | 2/2004 | Jaunakais et al. |
| 2002/0000414 A1 | 1/2002 | Kroll |

OTHER PUBLICATIONS

James Kalman Kearns, "Field Portable Methods for the Determination of Arsenic in Environmental Samples", Open Access Dissertations, Sep. 2010, 198 pages, University of Massachusetts Amherst.

James K. Kearns et al., "Expanding Quantification of Arsenic in Water to 0 μg L-1 with a Field Test Kit: Substituting 0.4% MA/ Silver Nitrate as the Colorimetric Reagent; Employing Digital Image Analysis", Water Air Soil Pollut, 2018, 7 pages, Springer International Publishing AG, part of Springer Nature.

*Primary Examiner* — Jennifer Wecker
*Assistant Examiner* — Kathryn Elizabeth Limbaugh
(74) *Attorney, Agent, or Firm* — Ference & Associates LLC

(57) ABSTRACT

An embodiment provides a method for measuring arsenic in a sample, showing marked increase in sensitivity over previous methods including: preparing a compound of metal-plated zinc and zinc; introducing the compound to an acidified sample, wherein the sample contains an amount of arsenic, wherein the compound reduces the amount of arsenic to produce arsine gas; wherein sufficient hydrogen gas is produced to purge the sample solution; wherein the arsine gas is completely purged from the sample and captured on a test pad, wherein the pad comprises mercuric bromide, wherein the capturing produces a color change of the pad; and measuring the amount of arsenic in the sample by measuring the color change of the pad. Other aspects are described and claimed.

19 Claims, 3 Drawing Sheets

50 ppb with nickel plated zinc method 50 ppb with nickel plated zinc method

REDUCING AGENT FOR ARSENIC MEASUREMENT

BACKGROUND

This application relates generally to measuring arsenic in a sample, and, more particularly, to the measurement of arsenic using a metal-plated zinc.

Arsenic is a naturally occurring component found in water. Arsenic may be introduced into water sources from rock or sediment. Arsenic may also be introduced through human activity. Mining, pesticides, manufacturing, or the like may introduce arsenic into groundwater. Arsenic may be toxic to animals even at low levels. Arsenic is also a known carcinogen. Treatment facilities require careful measurement and monitoring of arsenic levels. Regulatory agencies set limits for arsenic and detection at low concentrations allow treatment facilities to comply with regulations.

Current commercially available test kits for field use employ the Gutzeit test wherein zinc metal is added to an acidified sample that may contain arsenic. The arsenic in the sample is reduced to arsine gas by zinc which then must be purged from the aqueous sample by latent hydrogen production or mechanical stirring. A recent scientific study has shown the limitations of this type of test kit (See R.R. Reddy et al., 2019, Evaluation of arsenic field test kits for drinking water: Recommendations for improvement and implications for arsenic affected regions such as Bangladesh, *Water Research* 170 (2020) 115325). There still remains a need for improvements in cost effective field arsenic tests.

BRIEF SUMMARY

In summary, one embodiment provides a method for measuring arsenic in a sample, comprising: providing a compound of metal-plated zinc and zinc; introducing the compound to the sample, wherein the sample contains an amount of arsenic, wherein the compound reduces the amount of arsenic to produce arsine gas; capturing the arsine gas on a test pad, wherein the pad comprises mercuric bromide, wherein the capturing produces a color change of the pad; and measuring the amount of arsenic in the sample by measuring the color change of the pad.

Another embodiment provides a method for measuring arsenic in a sample, comprising: preparing a compound of a metal plated zinc and zinc, wherein the metal comprises a zero-valence metal; acidifying the sample using an acid; introducing the compound to the acidified sample, wherein the sample contains an amount of arsenic, wherein the compound reduces the amount of arsenic to produce arsine gas and produces hydrogen gas; capturing the arsine gas on a test pad, wherein the pad comprises mercuric bromide, wherein the capturing produces a color change of the pad; and measuring the amount of arsenic in the sample by measuring the color change of the pad.

A further embodiment provides a method for measuring arsenic in a sample comprising: preparing a compound, wherein the compound is selected from the group consisting of: a pure metal, and a mixture of pure metals and zinc, wherein the metals are in the zero valence state; acidifying the sample using an acid; introducing the compound to the acidified sample, wherein the sample contains an amount of arsenic, wherein the compound reduces the amount of arsenic to produce arsine gas and produces hydrogen gas; capturing the arsine gas on a test pad, wherein the pad comprises mercuric bromide, wherein the capturing produces a color change of the pad; and measuring the amount of arsenic in the sample by measuring the color change of the pad.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
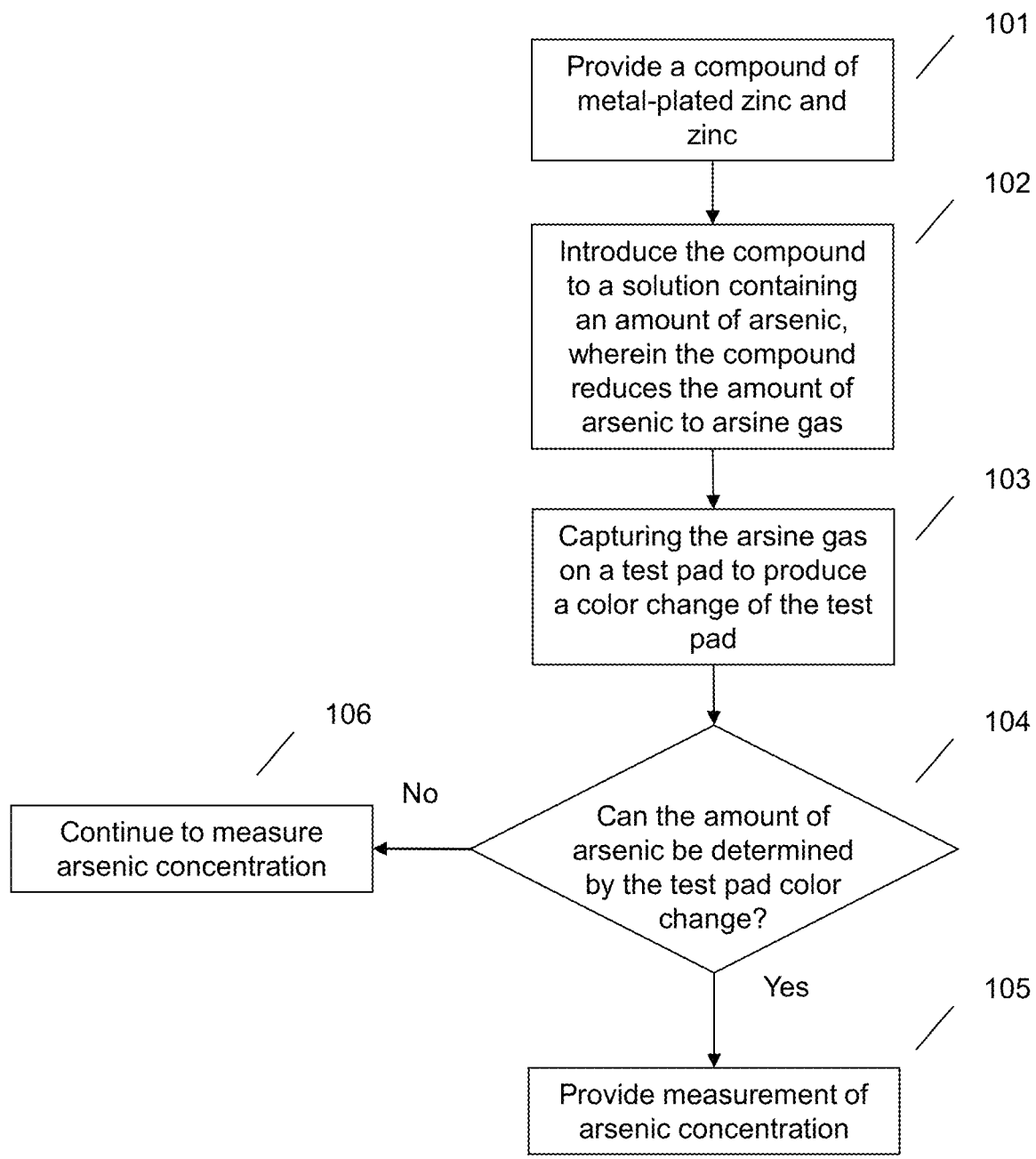
FIG. 1 illustrates a flow diagram of an example arsenic measuring system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example Conventional arsenic measurement and detection methods suffer from many disadvantages. For example, many arsenic test kits use a color indicator to be compared against known standard colors. At low concentrations of arsenic, these colors may be an off white or a very light yellow color. Distinguishing between arsenic concentrations at this light color can be difficult resulting in errors in distinguishing among off white or light yellow color at the low end of the concentration detection palate.

One method to detect arsenic uses the Gutzeit test. This test was introduced in the late 1800's. Further arsenic test kits have been introduced into the market, however, the method remains similar. The chemistry of the arsenic test remains the same. For example, an arsenic test may require inorganic arsenic in an aqueous form to be reduced to arsine gas. The arsine gas must then be purged from the aqueous solution. The purged gas may then be captured on a test strip. The color of the test strip indicates a presence or concentration of arsenic present in the sample.

Conventional arsenic measurement may require stirring. In other words, a sample with arsenic for measurement may require a physical agitation or stirring apparatus. The stirring may be needed to move the arsine gas to a test pad. Conventional methods may not capture all arsine gas upon the test strip. This inefficiency may lead to false negative or incorrect low reading of arsenic presence in a sample. What is needed is a reliable and field usable test for arsenic that captures arsine gas upon a test strip in a more completely.

Accordingly, an embodiment provides a method and system for measuring arsenic using a reducing agent. In an embodiment, a dual action method may be used that reduces arsenic to arsine gas and produces hydrogen gas in sufficient amounts to purge the arsine gas from the sample completely. In an embodiment, a metal may be plated upon zinc, or may be in the zero state free from zinc. The metal may be nickel, copper, tin, silver, iron, or the like, and be in a pure state or in a mixture with one another. The metal may be in a zero-valence state. The metal may be plated upon the zinc using electrolysis. The metal-plated zinc, such as nickel-plated zinc, may be combined with zinc to form a compound. The nickel-plated zinc and/or zinc may be introduced to a sample containing an amount of arsenic. In an embodiment, the zinc may predominantly reduce arsenic to arsine gas. The nickel-plated zinc may predominantly produce hydrogen gas. The hydrogen gas may be produced vigorously and eliminate the need for a mechanical stirring or agitation. The produced arsine gas may be captured upon a test pad. The test pad may comprise mercuric bromide. The color change of the test pad may correlate to the amount of arsenic in the sample. In an embodiment, the nickel-plated zinc may cause a color shift on a calibration curve of standards to a darker color of the test pad. The darker color, or more robust capture of arsine gas may allow for more accurate arsenic measurement and at lower arsenic concentrations.

The illustrated example embodiments will be best understood by reference to the figures. The following description is intended only by way of example, and simply illustrates certain example embodiments.

Referring to FIG. 1, an example method and system for detection of arsenic in solution is illustrated. In an embodiment, a compound of nickel-plated zinc and zinc may be prepared. The compound may be introduced into a sample in which the sample may contain an amount of arsenic. The arsenic may be reduced to arsine gas. The arsine gas may be capture on a test pad. A color change of the test pad may measure the presence or concentration of the amount of arsenic in the sample.

At 101, in an embodiment, a compound may be prepared. The compound may contain a metal, a metal plated with another metal, or a combination thereof. For example, the plating may be a metal such as cobalt, nickel, tin, iron, silver or other metal that can be plated on zinc actively or passively. For ease of readability, nickel may be used as an exemplar, however, other metal plating may be used. The compound may contain a nickel-plated zinc, zinc, or a combination thereof. The nickel plating of the zinc may be performed by electrolysis. In other words, an electrochemical reaction may place nickel upon the surface of the zinc. The plating may be complete and encapsulate the zinc. Alternatively, the nickel plating may be a portion of the surface of the zinc. In an embodiment, the nickel may be approximately 100 mesh particle in size. In an embodiment, nickel may be plated upon zinc using approximately 2 mg/g (2 milligrams nickel for every 1 gram of zinc). This nickel-plated zinc is then mixed with un-plated zinc at a ratio of between 1 to 2 parts to 20. In an embodiment, a combination of nickel-plated zinc and zinc may be prepared. The metal and plated metal may be in the form of small chunks, granules, or fine powder. The ratio of metal to metal plated pieces may vary. The size of the metal and ratio may be adjusted to properly produce hydrogen gas. In an embodiment, another metal may be used for plating, such as copper. In embodiment, the metal may be in a zero-valence state. In other words, a valence state of +2 or +3, wherein the metal is a soluble salt may not be not preferred.

In an embodiment, the compound of nickel-plated zinc and zinc may be referred to as dual action. For example, the zinc may reduce the arsenic, and the nickel may purge the sample solution with hydrogen to remove arsine gas. Additionally, the process of stirring the sample solution may be eliminated. In other words, combination of the nickel and zinc allows for a more sensitive measurement and detection of arsenic in a sample solution free from stirring technique variation.

At 102, in an embodiment, the compound may be introduced into a solution or sample. In an embodiment, the sample may be acidified with hydrochloric acid, sulfamic acid, or other suitable acid. The compound may comprise the nickel-plated zinc. The sample solution may contain an amount of arsenic. The sample solution may be an aqueous sample which may include a sample from a water treatment facility, natural body of water, industrial process facility, a holding tank, a processing tank, a pipe, or the like. The sample solution may be in a continuous flow, a standing volume of liquid, or any combination thereof. The nickel-plated zinc and/or zinc may have a dual action. In an embodiment, the zinc may reduce the arsenic to arsine gas. In an embodiment, the nickel may purge the sample solution with hydrogen to remove arsine gas. Proper purging of the arsine gas may result in a more accurate measurement as more arsine gas contact or captured by the test pad. In an embodiment, sulfamic acid may be added to the reaction. The sulfamic acid may be in the form of a liquid, powder, or powder pillow. The sulfamic acid may be used if the sample volume is larger, for example when increasing the volume from 50 milliliters to 75 milliliters, to maintain an acidic condition.

In an embodiment, a sample solution may be placed in a reaction vessel for arsenic testing. In one embodiment, the sample solution may be introduced to the compound, for example, a test chamber of the measurement device. In an embodiment, the measurement device may be a hand held device. Alternatively, the measurement device may be a larger bench top device. The test for arsenic may be performed in the field using a test kit, portable equipment, or the like. Introduction of the sample solution into the measurement device may include placing or introducing the solution into a test chamber manually by a user or using a mechanical means, for example, gravity flow, a pump, pressure, fluid flow, or the like. For example, a water sample for arsenic testing may be introduced to a measurement or test chamber using a pump. In an embodiment, valves or the like may control the influx and efflux of the solution into or out of the one or more chambers, if present. Alternatively, the measurement device may be connected directly to a treatment or characteristic measuring system.

Additionally or alternatively, the measurement device may be present or introduced in a volume of the solution.

The measurement device is then exposed to the volume of solution where it may perform measurements. The system may be a flow-through system in which a solution and/or reagents are automatically mixed and measured. Once the sample is in contact with the measurement system, the system may measure the amount of arsenic of the sample, as discussed in further detail herein. In an embodiment, the measurement device may include one or more chambers in which the one or more method steps may be performed.

At 103, in an embodiment, the method and system may measure an amount of arsenic in a sample solution using a change of color of a test pad. In an embodiment, the amount of arsenic may be reduced by the zinc to arsine gas. In an embodiment, the nickel or nickel plating allows for proper purging of the arsine gas such that the arsine gas may contact a test pad. The test pad may contain mercuric bromide. The reaction of the arsine gas with the mercuric bromide pad causes a color change of the test pad. For example, a lower amount of arsenic in a sample solution may produce an off white or light yellow or yellow color. As another example, a higher amount of arsenic in a sample solution may produce a light brown, brown, or dark brown color. Intermediate amounts of arsenic produce color shades between yellow and brown.

Figure 2:
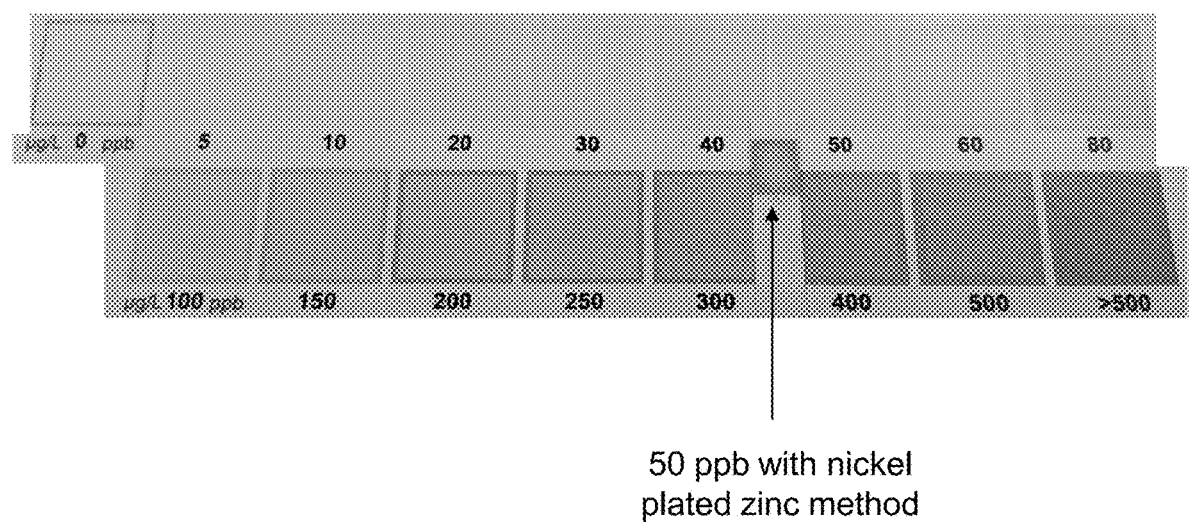
FIG. 2 illustrates an example shift to a darker color of a calibration curve of a test pad for arsenic measurement.

Referring to FIG. 2, conventional methods of arsenic detection may be difficult to visually determine the shade of an off white to light yellow color hue making determination of a lower amount of arsenic in a sample solution difficult to determine by the human eye, or even using equipment sensitive to color. For example, in FIG. 2 a series of conventional arsenic detection kit test pads (large squares) are shown with a test pad using the nickel-plated zinc shown as an inset (small square). The conventional method shows a range of detected arsenic from 0 parts per billion (ppb) as white in color, to 50 ppb as light yellow in color, to 200 ppb as a yellow, and 500 ppb as a reddish-brown. Note the 50 ppb nickel-plated zinc causes a color change of the test pad similar to a 300-400 ppb color observed in a conventional test. In an embodiment, the use of the dual action nickel-plated zinc results in a test pad signal demonstrating a signal of 2-6 times greater of a signal at an arsenic concentration of 50 ppb using current commercially available methods. The nickel or nickel plating allows a production of hydrogen gas. The nickel may not interfere with the reduction of arsenic to arsine gas. The production of hydrogen gas allows better transfer of the arsine gas to the test pad. In an embodiment, nickel may be plated upon zinc using approximately 2 mg/g (2 milligrams nickel for every 1 gram of zinc). This nickel-plated zinc is then mixed with un-plated zinc at a ratio of between 1 to 2 parts to 20. Other ratios may be used depending on specific applications. In an embodiment, the produced arsine gas is better purged and made available to the test pad. In turn, a more accurate measurement or arsenic may be made, and a deeper color of the test pad observed. In other words, an amount of arsenic may produce a darker color of a calibration curve upon reaction of the test pad. A darker test pad color may facilitate a more accurate comparison to colors representing standard arsenic concentration for the arsenic test.

At 104, in an embodiment, the system and method may determine if an amount of arsenic in solution may be measured. In an embodiment, the presence of arsenic in an aqueous solution may cause a darker color of the test pad to be observed. Therefore, the observed color, of a test pad testing a solution containing an amount of arsine gas may be correlated to a known concentration color of a test pad of the arsenic in the aqueous or sample solution. In other words, the amount of arsenic determination may be made from human observation or automated using instruments capable of determining the color of the test pad.

Alternatively or additionally, the amount of arsenic or arsenic concentration measurement may be at periodic intervals set by the user or preprogrammed frequencies in the device. Measurement of arsenic by a device allows for real time data with very little human involvement in the measurement process. Cleaning of the measurement or reaction chamber may be required at an unspecified time interval. A programmed calibration curve may be entered into the device.

A chamber, vessel, cell, chamber, or the like may contain an aqueous sample, the zinc, the metal-plated zinc, and associated reagents such as buffers and/or additives. A device may contain one or more bottles/containers of reagents and/or metal which contain necessary reagents. The reagents contained in the one or more bottles or containers may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, metal, and related reagents.

The measurement of the amount of arsenic may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels. For example, an analyte measuring device may use a relay coupled to an electrically actuated valve, or the like.

At 106, in an embodiment, if an amount of arsenic cannot be determined, the system may continue to measure an amount of arsenic from the same or a different volume of a sample. In an embodiment, a new test pad and associated reagents, such as the nickel-plated zinc and zinc, may be used. Additionally or alternatively, the system may output an alarm, log an event, or the like.

At 105, if an amount of arsenic can be determined, the system may provide a measurement of the amount of arsenic in solution. In an embodiment, a color of the test pad may be correlated to known test pad concentration, and results and measurements logged. The system may connect to a communication network. The system may alert a user or a network. This alert may occur whether an arsenic measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if an amount of arsenic or arsenic concentration reaches a threshold. Alarms or logs may be analyzed in real-time, stored for later use, or any combination thereof.

The various embodiments described herein thus represent a technical improvement to conventional arsenic measurement techniques. Using the techniques as described herein, an embodiment may use a reducing agent, such as nickel-plated zinc, to measure an amount of arsenic in solution. The methods and system described herein provide a more accurate method with higher sensitivity for measuring arsenic in an aqueous or liquid solution.

Figure 3:
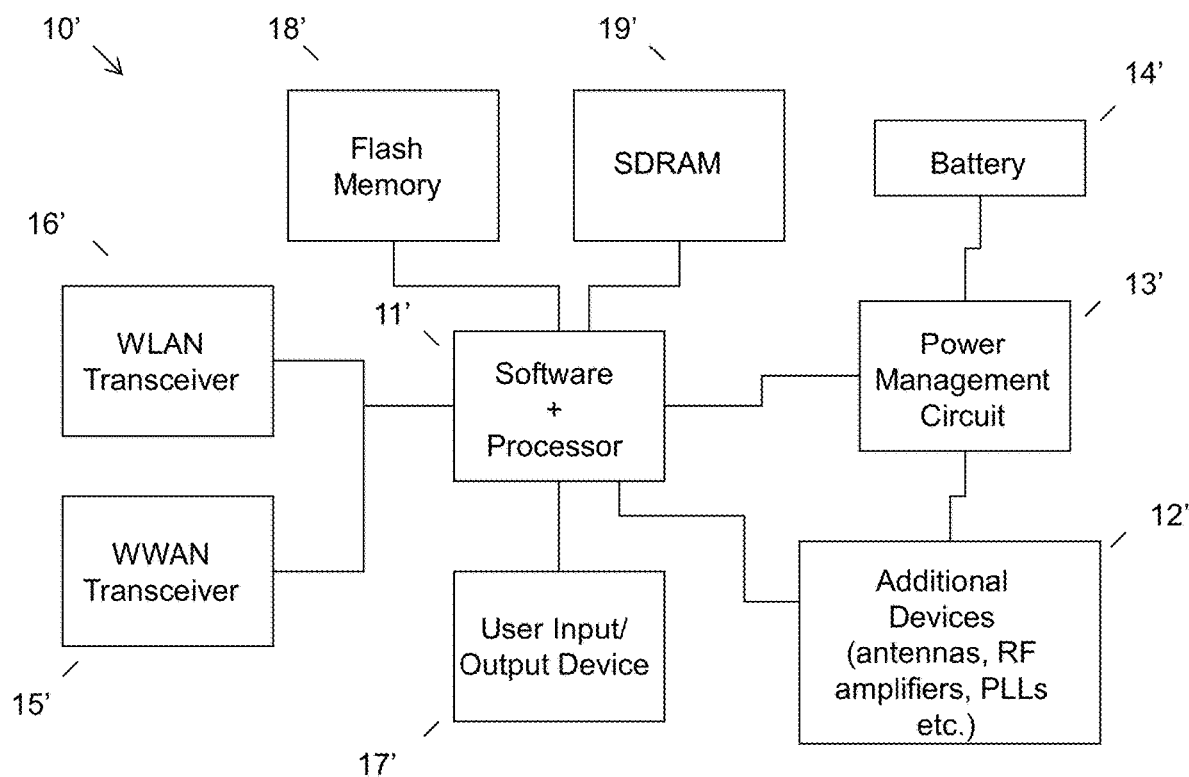
FIG. 3 illustrates an example of computer circuitry.

While various other circuits, circuitry or components may be utilized in information handling devices, with regard to an instrument for measurement of arsenic according to any one of the various embodiments described herein, an example is illustrated in FIG. 3. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of arsenic of an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring arsenic in a sample, comprising:
    providing a compound of metal-plated zinc and zinc;
    introducing the compound to the sample, wherein the sample contains an amount of arsenic, wherein the compound reduces the amount of arsenic to produce arsine gas;
    capturing the arsine gas on a test pad, wherein the test pad comprises mercuric bromide, wherein the capturing produces a color change of the pad; and
    measuring the amount of arsenic in the sample by measuring the color change of the test pad.

2. The method of claim 1, wherein the method further comprises preparing the compound of metal-plated zinc, wherein the preparing comprises electrolysis to plate the metal upon the zinc.

3. The method of claim 1, wherein the metal-plated zinc is prepared at 2 milligrams of metal to 1 gram of zinc.

4. The method of claim 1, wherein the metal is in a zero-valence state.

5. The method of claim 1, wherein the metal plating produces hydrogen gas which sufficiently purges arsine gas from the sample, without adversely affecting arsenic reduction to arsine.

6. The method of claim 1, further comprising adding sulfamic acid to reduce the amount of arsenic.

7. The method of claim 1, wherein the metal-plated zinc produces a darker color of a calibration curve to the color change of the test pad.

8. The method of claim 1, wherein the color change of the test pad correlates to the amount of arsenic in the sample.

9. The method of claim 1, wherein a physical stirring of the sample is not required during the reduction.

10. The method of claim 1, wherein the sample comprises a water sample.

11. A method for measuring arsenic in a sample, comprising:
   preparing a compound of a metal plated zinc and zinc, wherein the metal comprises a zero-valence metal;
   acidifying the sample using an acid;
   introducing the compound to the acidified sample, wherein the sample contains an amount of arsenic, wherein the compound reduces the amount of arsenic to produce arsine gas and produces hydrogen gas;
   capturing the arsine gas on a test pad, wherein the test pad comprises mercuric bromide, wherein the capturing produces a color change of the test pad; and
   measuring the amount of arsenic in the sample by measuring the color change of the test pad.

12. The method of claim 11, wherein the preparing comprises electrolysis to plate the metal upon the zinc.

13. The method of claim 11, wherein the metal-plated zinc is prepared at 2 milligrams of metal to 1 gram of zinc.

14. The method of claim 11, wherein the metal plating produces hydrogen gas which sufficiently purges arsine gas from the sample, without adversely affecting arsenic reduction to arsine.

15. The method of claim 11, further comprising adding sulfamic acid to reduce the amount of arsenic.

16. The method of claim 11, wherein the metal-plated zinc produces a darker color of a calibration curve to the color change of the test pad.

17. The method of claim 11, wherein the color change of the test pad correlates to the amount of arsenic in the sample.

18. The method of claim 11, wherein a physical stirring of the sample is not required during the reduction.

19. A method for measuring arsenic in a sample comprising:
   preparing a compound, wherein the compound is selected from the group consisting of: a pure metal, and a mixture of pure metals and zinc, wherein the zinc is plated with the pure metal, and wherein the pure metals are in the zero valence state;
   acidifying the sample using an acid;
   introducing the compound to the acidified sample, wherein the sample contains an amount of arsenic, wherein the compound reduces the amount of arsenic to produce arsine gas and produces hydrogen gas;
   capturing the arsine gas on a test pad, wherein the pad comprises mercuric bromide, wherein the capturing produces a color change of the test pad; and
   measuring the amount of arsenic in the sample by measuring the color change of the test pad.

* * * * *